US009028752B2

(12) United States Patent
 Malin

(10) Patent No.: US 9,028,752 B2
(45) Date of Patent: May 12, 2015

(54) DEVICE FOR STORING AND HANDLING PETRI DISHES, STORAGE DEVICE AND STORAGE SLOT FOR LABORATORY OBJECTS

(75) Inventor: Cosmas G. Malin, Mauren (LI)

(73) Assignee: Liconic AG, Mauren (LI)

(*) Notice: Subject to any disclaimer, the term of this patent is extended or adjusted under 35 U.S.C. 154(b) by 52 days.

(21) Appl. No.: 13/360,226

(22) Filed: Jan. 27, 2012

(65) Prior Publication Data

US 2012/0251275 A1   Oct. 4, 2012

(30) Foreign Application Priority Data

Jan. 28, 2011 (CH) .......................................... 151/11
May 6, 2011 (CH) .......................................... 783/11

(51) Int. Cl.

| C12M 1/22 | (2006.01) |
|---|---|
| C12M 1/34 | (2006.01) |
| C12M 1/26 | (2006.01) |
| G01N 1/28 | (2006.01) |
| G01N 35/00 | (2006.01) |
| C12M 1/00 | (2006.01) |
| C12M 1/36 | (2006.01) |
| G01N 35/02 | (2006.01) |
| G01N 35/04 | (2006.01) |

(52) U.S. Cl.
CPC ................ C12M 23/10 (2013.01); *C12M 1/36* (2013.01); *G01N 35/025* (2013.01); *G01N 2035/0441* (2013.01); G01N 35/0099 (2013.01); *G01N 2035/0425* (2013.01); C12M 23/50 (2013.01)

(58) Field of Classification Search
CPC ... C12M 23/50; C12M 23/52; G01N 35/0099
See application file for complete search history.

(56) References Cited

U.S. PATENT DOCUMENTS

| 3,844,896 | A |   | 10/1974 | Sharpe |   |
|---|---|---|---|---|---|
| 4,090,921 | A | * | 5/1978 | Sawamura et al. | ......... 435/286.2 |
| 4,166,006 | A | * | 8/1979 | Hertl et al. | .................... 435/244 |
| 4,287,301 | A |   | 9/1981 | Astle |   |
| 5,036,001 | A |   | 7/1991 | Gork et al. |   |
| 6,478,524 | B1 |   | 11/2002 | Malin |   |
| 6,843,962 | B2 |   | 1/2005 | Haslam et al. |   |
| 6,998,094 | B2 |   | 2/2006 | Haslam et al. |   |
| 2003/0044321 | A1 |   | 3/2003 | Haslam et al. |   |

(Continued)

FOREIGN PATENT DOCUMENTS

| DE | 37 20 733 A1 | 10/1988 |
|---|---|---|
| WO | 2008/083439 A1 | 7/2008 |

OTHER PUBLICATIONS

Switzerland Search report from counterpart application No. CH 0151/11, mail date is May 10, 2011.

*Primary Examiner* — P. Kathryn Wright
(74) *Attorney, Agent, or Firm* — Greenblum & Bernstein, P.L.C.

(57) ABSTRACT

A device for storing and handling Petri dishes having a base with a base wall arranged on a circumference of the base, and a lid. The device includes a storage device structured and arranged for storing the Petri dishes in an upside-down orientation so that respective lids are oriented below their respective bases, an inspection device structured and arranged for automatic inspection of the Petri dishes without their respective lids, and a transfer device structured and arranged for transferring the Petri dishes between the storage device and the inspection device. The transfer device includes a gripper, with which a respective Petri dish without the lid can be grasped laterally on the base wall.

45 Claims, 10 Drawing Sheets

(56) References Cited

U.S. PATENT DOCUMENTS

| | | |
|---|---|---|
| 2003/0044991 A1 | 3/2003 | Haslam et al. |
| 2003/0085368 A1* | 5/2003 | Kesil et al. ............... 250/559.36 |
| 2004/0115101 A1 | 6/2004 | Malin |
| 2004/0213651 A1 | 10/2004 | Malin |
| 2006/0115889 A1* | 6/2006 | Nakashima et al. ....... 435/286.2 |
| 2008/0231152 A1 | 9/2008 | Malin |
| 2009/0175763 A1 | 7/2009 | Malin |
| 2009/0245986 A1 | 10/2009 | Malin |
| 2010/0173416 A1* | 7/2010 | Gupta et al. .................. 435/395 |
| 2010/0183408 A1 | 7/2010 | Malin |
| 2010/0211211 A1* | 8/2010 | Nedu et al. .................... 700/218 |
| 2011/0085409 A1 | 4/2011 | Malin |

\* cited by examiner

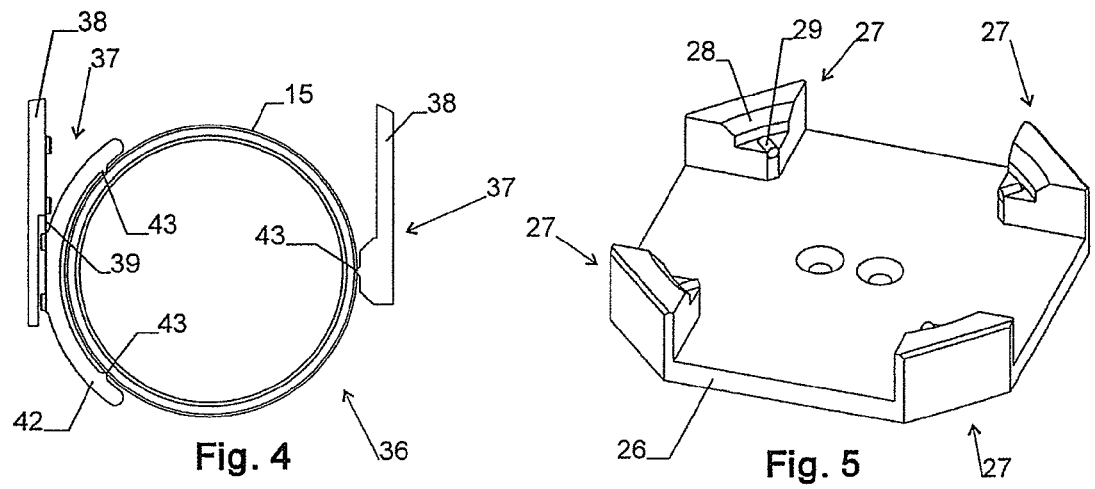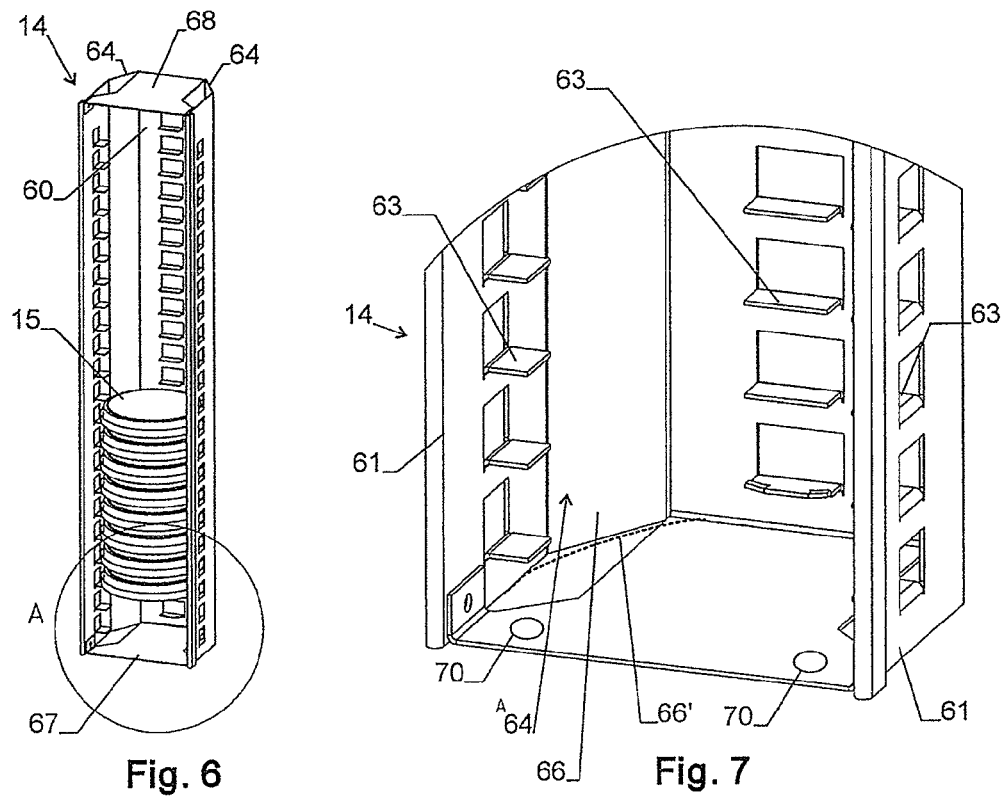

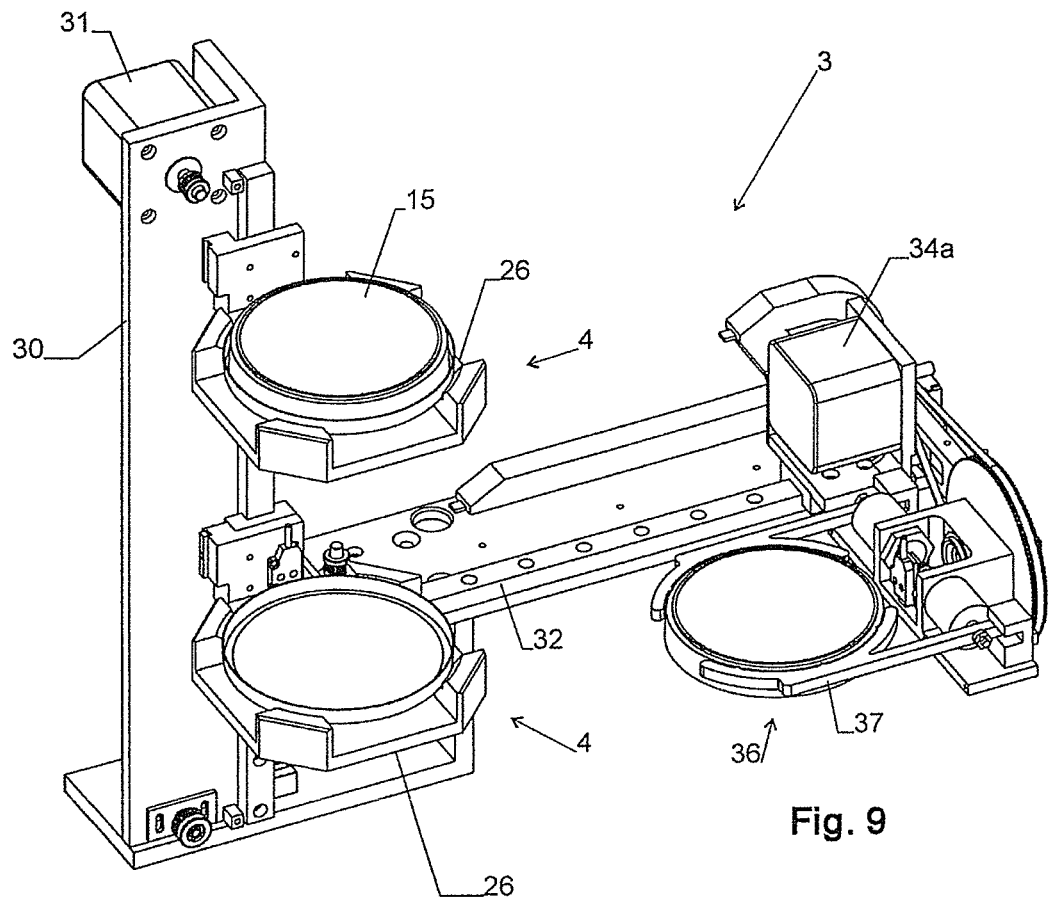
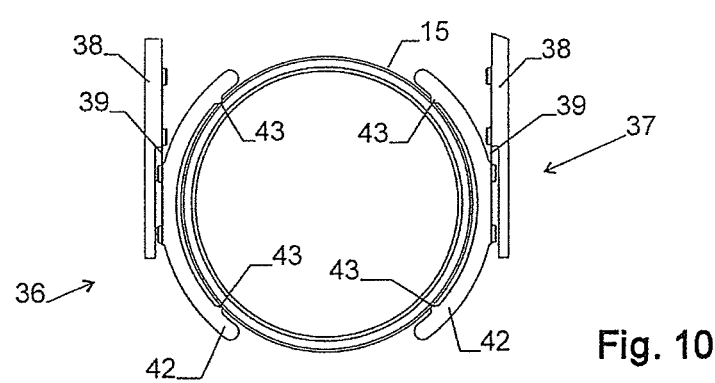

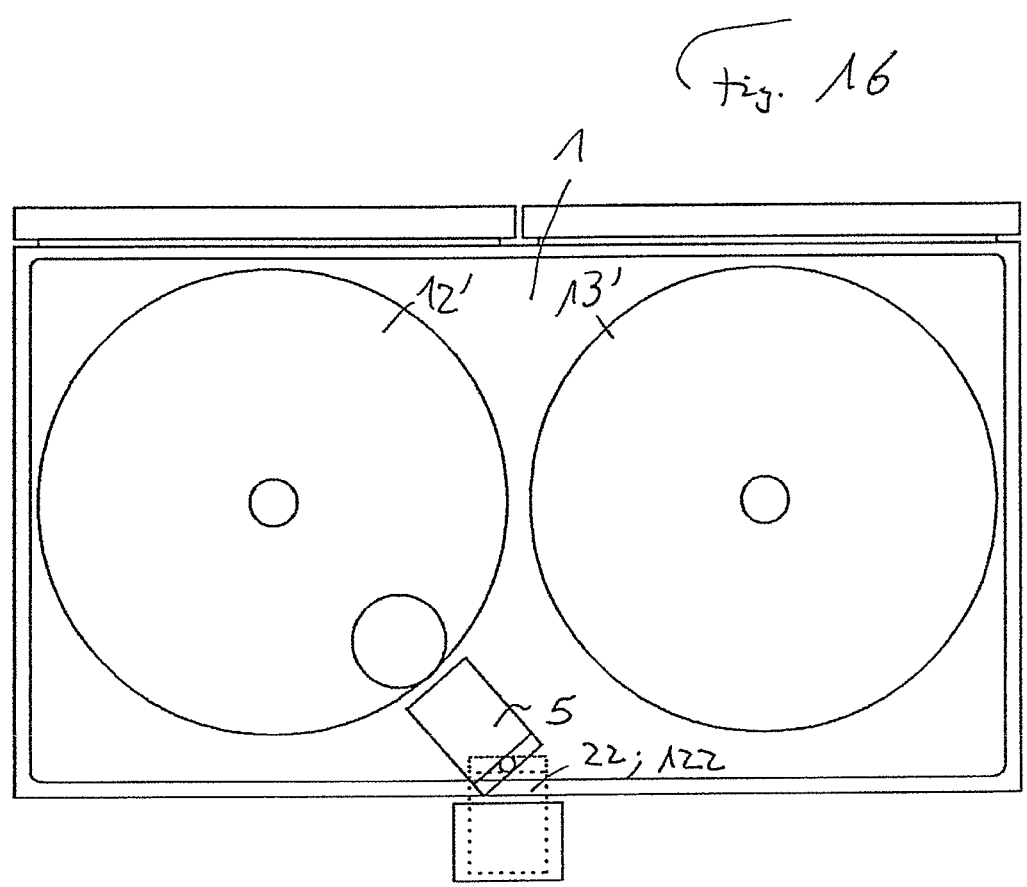

DEVICE FOR STORING AND HANDLING PETRI DISHES, STORAGE DEVICE AND STORAGE SLOT FOR LABORATORY OBJECTS

CROSS-REFERENCE TO RELATED APPLICATIONS

The instant application claims priority under 35 U.S.C. §119(a) to Swiss Application No. 0151/11, filed on Jan. 28, 2011 and to Swiss Application No. 0783/11, filed on May 6, 2011, the disclosures of which are expressly incorporated by reference herein in their entireties.

BACKGROUND OF THE INVENTION

1. Field of the Invention

The invention relates to a device for storing and handling laboratory objects, in particular Petri dishes. Furthermore, the invention relates to a storage device and a storage rack as well as a laboratory device.

2. Discussion of Background Information

Petri dishes are flat, round, transparent dishes with spanning lid, which are widely used in biology, medicine or chemistry. Petri dishes are thereby used for the cultivation of microorganisms and cell cultures. A flat layer of a gel-like culture medium is placed into the Petri dish and supplies the growing microorganisms with water and the necessary nutrients.

Application-specific microorganisms are locally introduced into the culture medium. Subsequently, the Petri dishes are usually incubated with the lid downwards and the culture medium upwards. With this storage, the weight of the plate bears on the lid, whereby the closure between the lid and dish is improved. Excess water does not form on the culture medium, but preferably collects on the lid.

During the incubation period, the growth of the cultures is visually inspected several times. In applications in which large numbers of plates are used, there is a need for an automation of the process. Respectively, one Petri dish is thereby removed from the incubator or the storage device and fed to an inspection device according to certain time specifications. For the inspection, the plates should be fed to the inspection device with the culture medium downwards.

To transfer the Petri dishes between the storage device and the inspection device, a transfer device is required. Usually, this has a pivoted arm, which is arranged on a wall of the incubation chamber or storage device. A Petri dish is grasped by a vacuum suction device, which is arranged on the outer end of the pivoted arm, and is removed from the incubator by a rotary motion of 180 degrees and rotated at the same time. In the inspection device, the vacuum suction device must be removed for the inspection.

Furthermore, storage racks are known for storing laboratory objects, which racks respectively provide space for several laboratory objects one above the other.

SUMMARY OF EMBODIMENTS OF THE INVENTION

In a first aspect of the invention the aim is to be attained of providing a device for the storage and handling of Petri dishes, which permits an efficient handling of the Petri dishes.

This aim is attained by the device for storing and handling Petri dishes having a base with a base wall arranged on a circumference of the base, and a lid, the device comprising a storage device for storing the Petri dishes in an upside-down orientation so that respective lids are oriented below their respective bases, an inspection device for the automatic inspection of Petri dishes their respective lids, and a transfer device structured and arranged for transferring the Petri dishes between the storage device and the inspection device, wherein the transfer device comprises a gripper structured and arranged to laterally grasp a respective base wall. Accordingly, the transfer device has a gripper, with which respectively one Petri dish without the lid can be grasped laterally on the sidewalls of the base. The advantage of this solution lies in that the gripper, in contrast to a vacuum suction device, acts on the Petri dish essentially only laterally, but not centrally, so that the Petri dish remains more easily accessible for the inspection.

In embodiments, the transfer device further comprises at least one transfer station structured and arranged for holding the respective Petri dish in the upside-down orientation, from which the gripper can grasp the respective base wall.

In embodiments, the transfer device further comprises a turning drive structured and arranged to rotate the gripper with a held base of a Petri dish above the lid lying in the transfer station.

In further embodiments, the turning device is structured and arranged to rotate the gripper by more than 90°.

In additional embodiments, the transfer device further comprises a lift drive structured and arranged to displace the gripper vertically relative to the transfer station.

In yet further embodiments, the transfer device further comprises a horizontal drive structured and arranged to move the gripper to and from the inspection device for inspection.

In embodiments, the at least one transfer station comprises two transfer stations, both of which are moveable.

In further embodiments, the device further comprises a common lift drive for the two transfer stations.

In additional embodiments, the transfer device is structured and arranged to hold the base with the gripper during the inspection by the inspection device.

In yet further embodiments, the storage device comprises a plurality of storage locations structured and arranged for storing the Petri dishes in the upside-down orientation so that respective lids are oriented below their respective bases, and a handling device structured and arranged to transport the Petri dishes between the storage locations and the transfer device.

In embodiments, the handling device is structured and arranged to transfer the Petri dishes between the storage locations and the transfer station without turning over the Petri dishes.

In further embodiments, the storage locations are formed by a plurality of storage racks, wherein each storage rack has several storage locations one above the other.

In additional embodiments, the device further comprises at least one carousel, wherein the storage shafts are arranged on the at least one carousel.

In yet further embodiments, the handling device comprises two vertically moveable carriages.

In embodiments, the device further comprises a common lift column, wherein the carriages are arranged above one another on the common lift column.

In further embodiments, the gripper comprises two fingers moveable with respect to one another, and wherein the fingers have a plurality of elevations respectively directed against one another for acting on the base wall of the Petri dish.

In additional embodiments, the plurality of elevations comprise three elevations.

In yet further embodiments, at least one of the fingers comprises a spring mounting bearing a base part, wherein at least one of the plurality of elevations is arranged on the base part.

In further embodiments, the at least one transfer station further comprises at least one fixing element for the lid of the Petri dish, which is structured and arranged to temporarily fix the lid in a controlled manner.

In additional embodiments, the at least one fixing element comprises an arched fixing element.

In yet further embodiments, the at least one transfer station further comprises a transfer table, and wherein the at least one fixing element is structured and arranged on the transfer table.

In embodiments, the at least one fixing element comprises two fixing elements.

In further embodiments, the transfer device comprises a common carrier plate on which the at least one transfer station and the gripper are arranged.

In additional embodiments, the at least one transfer station comprises two transfer stations.

In yet further embodiments, the common carrier plate is a one-piece carrier plate.

In embodiments, the common carrier plate is an L-shaped carrier plate.

In further embodiments, the transfer device further comprises an optical sensor in the region of the gripper that can be switched off temporarily in a controlled manner, which sensor is structured and arranged for detecting a presence or absence of the base in the gripper.

In additional embodiments, the at least one transfer station comprises a sensor structured and arranged for detecting a presence or absence of the lid in the transfer station.

In yet further embodiments, the gripper is structured and arranged such that its base position is a grasping condition.

In embodiments, the at least one fixing element is structured and arranged such that its base position is an open, non-fixing position.

In further embodiments, the gripper comprises at least two fingers, which are each structured and arranged on respective bodies, wherein the bodies are structured and arranged to be moved towards one another and away from one another in a controlled driven manner, and wherein each finger is attached to a respective body in a manner to be pivotable in a horizontal plane.

In additional embodiments, each finger is attached to a respective shaft, and is structured and arranged for centering itself automatically into an unpivoted base position.

In yet further embodiments, each finger is attached to the respective shaft by a rear side of each finger via a respective leaf spring.

In embodiments, wherein the fingers of the gripper are structured and arranged for an essentially punctiform contact with the Petri dish.

In further embodiments, the fingers comprise end regions, and the punctiform contact is provided by the of the end regions of the fingers.

In additional embodiments, the fingers comprise a base part, and an interchange part releasably attached to the base part, wherein the interchange part is structured and arranged to provide an essentially punctiform contact with the Petri dish.

In embodiments, the base part is formed of a light metal and the interchange part is formed of steel.

In further embodiments, the light metal comprises aluminum.

In additional embodiments, the steel comprises spring steel.

In yet further embodiments, the gripper is structured and arranged such that a size of an angle from a center of a grasping region to outermost contact parts of the fingers of the gripper, which are structured and arranged for contacting the base wall, is 80 to 120 degrees.

In embodiments, the angle is 85 to 100 degrees.

In further embodiments, the angle is approximately 90 degrees.

In additional embodiments, the device further comprises a handling device, and a transport arrangement located outside the storage device on a wall of the storage device. The storage device comprises a first auxiliary door on the wall of the storage device and a second auxiliary door on the wall of the storage device through which a supply or removal of Petri dishes into or out of the storage device can be carried out by the handling device. The transfer device is structured and arranged on the wall of the storage device.

In yet further embodiments, the second auxiliary door lies in a same vertical axis as the first auxiliary door.

In embodiments, the second auxiliary door is arranged below the first auxiliary door.

In further embodiments, the transport arrangement comprises two lifting devices lying vertically one above the other and driven in a controlled manner, by which Petri dishes, independently of one another, can be lifted from or deposited on two conveyor belts arranged one above the other.

In additional embodiments, each of the two lifting device has a respective sensor by which a presence or absence of a Petri dish can be established.

In yet further embodiments, the device further comprises a common handling device, wherein the at least one carousel comprises two carousels arranged separately from one another and next to one another in the storage device, which can be served by the common handling device.

Additional aspects of the invention are directed to a laboratory device comprising the device, wherein the laboratory device comprises a control and two conveyor belts lying one above the other and driven in a controlled manner. The two conveyor belts are arranged and can be controlled to interact with the lifting devices in order to feed Petri dishes into the storage device of the device or to remove them therefrom.

Additional aspects of the present invention are directed to a storage device, comprising a substrate having at least one pin, at least one resilient tongue, and at least one storage rack. Each storage rack has a base and a plurality of storage locations structured and arranged for holding respectively one laboratory object one above the other, wherein in the base of each storage rack, at least one opening is structured and arranged, in which the at least one pin of the substrate engages, and wherein the at least one storage rack is held from above by the at least one resilient tongue.

In embodiments, the storage device further comprises at least one carousel, which forms the substrate for the at least storage rack, and wherein the at least one storage rack comprises a plurality of storage racks arranged in at least one circle on the at least one carousel.

In further embodiments, the storage device further comprises a center region, and wherein the at least one tongue comprises a plurality of tongues structured and arranged radially, and respectively attached to the center region.

In additional embodiments, the at least one tongue is flexibly biased and structured and arranged to press from above on the at least one storage rack.

Additional aspects of the present invention are directed to a storage rack comprising a rear wall, two sidewalls, and lateral storage compartments for holding Petri dishes being structured and arranged at least on the two sidewalls. The rear wall merges via respective transition regions into each sidewall, and the transition regions are at least one of rounded and running obliquely between the rear wall and the sidewall adjacent thereto.

In yet further embodiments, the transition region is rounded with a radius of curvature of at least 2 cm.

In embodiments, the radius of curvature is at least 5 cm.

In further embodiments, the transition region comprises an essentially flat section, which has an extension of at least 2 cm perpendicular to a longitudinal axis of the storage rack.

In embodiments, the rear wall comprises lateral storage compartments for holding the Petri dishes.

Preferably, the transfer device has a transfer station for holding a Petri dish with the lid downwards. From this, one Petri dish at a time without a lid is grasped by the gripper and lifted upwards so that the lid remains on the transfer station.

It is advantageous in this case if the transfer device has a turning drive, which is embodied such that the gripper with the held Petri dish is turned over vertically above the lid. It is shown that the risk of contamination can thus be reduced, in that drops that are detached, e.g., due to the air draft, during the turning of the Petri dish, fall downwards into the lid and are not deposited in an uncontrolled manner at other locations in the device.

In a further advantageous embodiment, the device has a lift drive, with which the gripper can be moved over the transfer station and vertically relative thereto, i.e., can be moved in a vertical translational motion. To this end, either the gripper or the transfer station, or both parts can be moved. Thanks to the vertical lift, a tilting of the base of the Petri dish held by the gripper in the lid thereof can be avoided.

As a rule, the storage device forms a plurality of storage locations for Petri dishes, and the device is embodied such that the Petri dishes are stored in the storage locations with the lid downwards. Furthermore, a handling device can be provided in addition to the transfer device in order to transport the Petri dishes to and fro between the storage locations and the transfer device. The handling device can be arranged at least in part in the storage device.

The storage locations for the Petri dishes are advantageously formed by several storage racks. Each of these storage racks has several storage locations one above the other, so that the Petri dishes can be stored as in a tower. In a particularly advantageous embodiment, these storage racks are arranged on a carousel, so that each of them can be brought to the handling device by rotating the carousel.

In a second aspect, the invention relates to a storage device for holding laboratory objects, in particular Petri dishes or microtitration plates. This storage device can be suitable in particular (but not solely) for use in the above-described device. The storage device should permit a simple assembly and disassembly of the storage racks. In embodiments, the storage device has at least one storage rack, wherein each storage rack has several storage locations for holding respectively one laboratory object one above the other. On the base of each storage rack at least one opening is arranged, which is engaged by at least one pin of a substrate of the storage rack. From above, the storage racks are held by a flexible tongue. By deformation of the tongue, a storage rack can be lifted, released from the pins and removed from the storage device.

In a third aspect, the invention relates to a storage rack for holding Petri dishes, which is suitable in particular (but not solely) for use in the device described above and is designed to permit a compact storage. The storage rack has a rear wall and two sidewalls. Supports for the peripheral accommodation of the Petri dishes are provided at least on the side walls, optionally also on the rear wall. The rear wall merges into the two sidewalls via two transition regions. Each transition region is rounded, or it runs obliquely to the rear wall and to the respectively adjacent sidewall. This embodiment, which takes into consideration the round design of Petri dishes, has the advantage that the storage racks can be arranged narrowly in a circle, for example, on a carousel, so that a storage with high spatial capacity is possible.

In a further aspect, the invention relates to a laboratory device, which is designed and provided for interaction with the device.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 4 illustrates an embodiment of a gripper;

FIG. 5 illustrates one of several supports of the transfer station;

FIG. 6 illustrates a storage rack for Petri dishes;

FIG. 7 illustrates a detail (circle A) of the storage rack of FIG. 6;

FIG. 9 illustrates a transfer device with two transfer stations one above the other;

FIG. 10 illustrates an alternative embodiment for the gripper according to FIG. 4;

FIG. 16 illustrates a further embodiment of the storage device.

DETAILED DESCRIPTION OF EMBODIMENTS OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
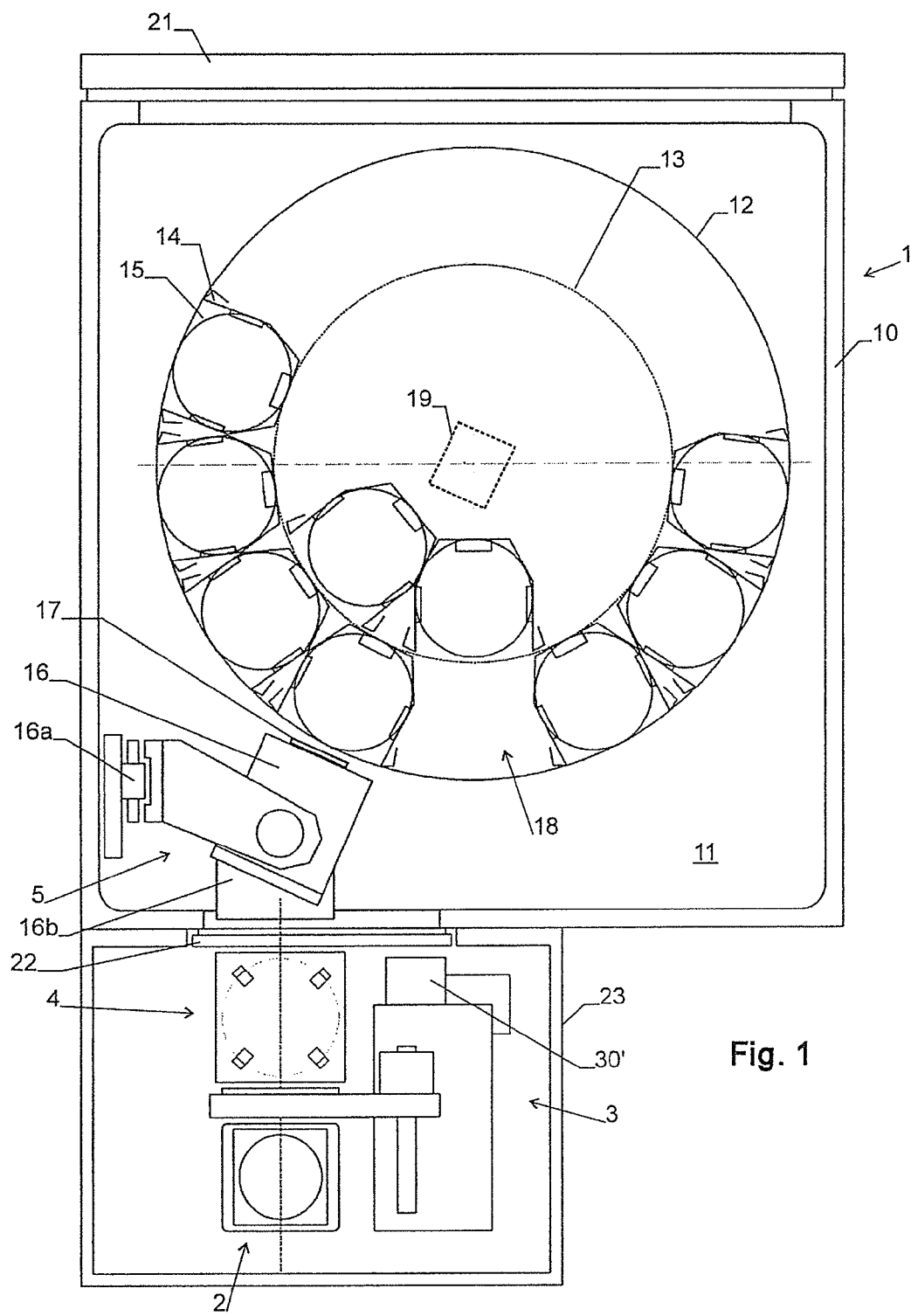
FIG. 1 illustrates a view of a system from above.

FIG. 1 shows a device for storing and handling Petri dishes 15 from above. It comprises a storage device 1, an inspection device 2, a transfer device 3, a transfer station 4 and a handling device 5. The structure and the function of these components are described in detail below.

The storage device 1 is preferably embodied as an incubator, i.e., as a climatic cabinet, in the interior of which a desired temperature and atmosphere can be maintained by a suitable air conditioning. The storage device 1 has a wall 10, which surrounds an interior 11. In the interior 11 two carousels 12 and 13, which can be rotated independently of one another, are arranged concentrically, which respectively bear a circle of storage racks 14, only a part of which is shown in FIG. 1. Each storage rack 14 forms a plurality of storage locations for Petri dishes 15 one above the other.

Furthermore, the handling device 5 is arranged in a corner of the interior 11, which handling device is used to transport the Petri dishes 15 to and fro between the storage locations and the transfer device 3. To this end, the handling device 5 has at least one carriage 16 that can be moved vertically on a lift column 16a, on which carriage 16 a scoop 17 is arranged that can be extended horizontally and pivoted about a vertical axis. This scoop 17 can be moved into the storage racks 14 in the swivel position shown in FIG. 1 in order to pick up or deposit, respectively, one Petri dish 15. Through a gap 18 in the outer circle of the storage racks 14, the scoop 17 can also access the storage locations of the storage racks of the inner circle. To this end, the carousel 12 with the outer circle of the storage racks 14 is rotated such that the gap 18 comes to rest in the region of the scoop 17. Optionally, an auxiliary device 19 can also be provided in the center of the inner carousel 13, which auxiliary device 19 supports the work of the scoop 17 and helps the scoop 17 to charge the storage locations of the inner circle.

As further indicated in FIG. 1, at least two carriages 16, 16b are arranged one above the other on the lift column 16a in the embodiment shown. In FIG. 1 the lower carriage 16b is thereby currently rotated towards the transfer station 4. The handling capacity can be increased by using several carriages 16, 16b that can be moved vertically independently of one another. The lower carriage 16b serves the lower half of the storage device 1, and the upper carriage 16 serves the upper half.

As can be further seen, in the embodiment shown the storage device 1 has a user door 21 as well as an auxiliary door 22 that can be automatically opened and closed. In order to transport a Petri dish 15 from the interior 11 outwards or in the reverse direction with the handling device 5, the auxiliary door 22 is opened.

Outside the storage device 1, e.g., a table 23 can be arranged, which bears the components described below. The table 23 can be attached to the outside of the storage device 1.

Figure 2:
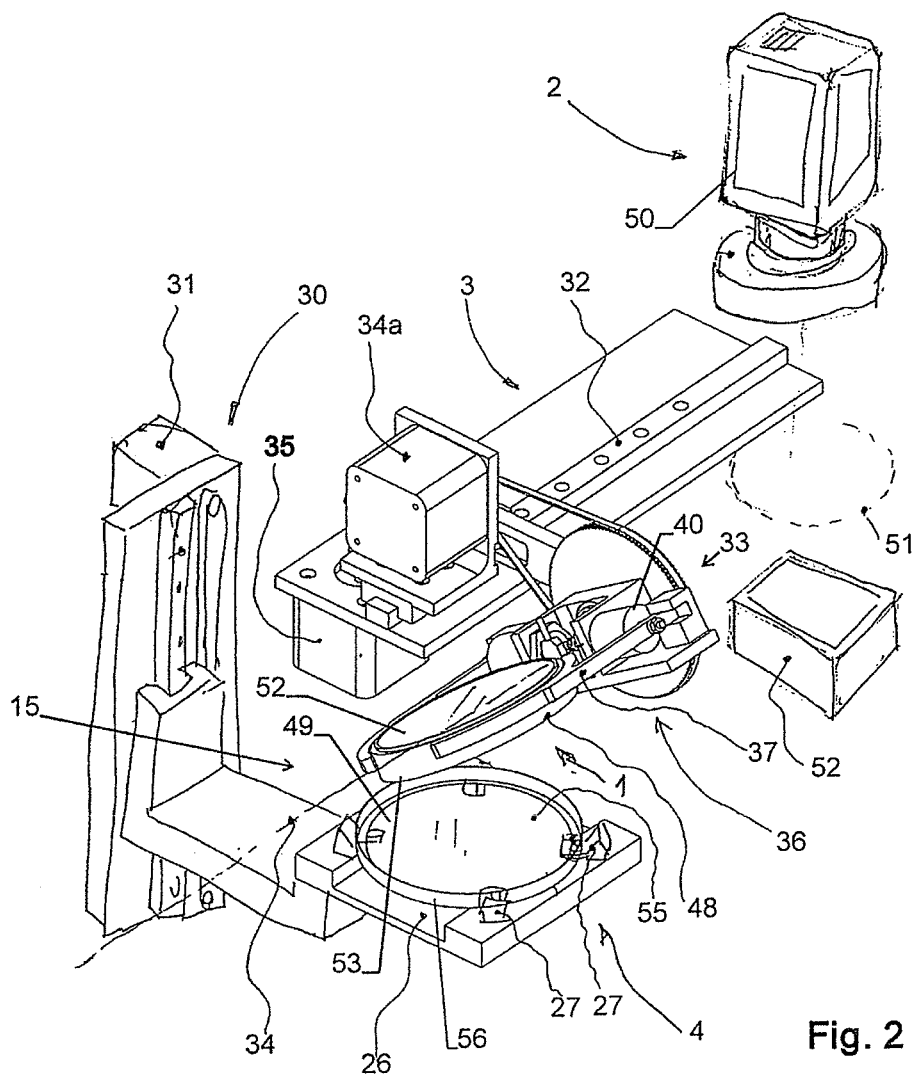
FIG. 2 illustrates a view of the transfer device and the adjacent components.

The transfer station 4, which is also shown in FIG. 2, is used to take at least one Petri dish 15 removed by the handling device 5 or to temporarily hold at least one Petri dish 15, which then is lifted by the handling device 5 and deposited into one of the storage locations in the storage device 1.

As shown in FIG. 2, the transfer station 4 comprises a transfer table 26, on which four supports 27 are arranged that are elevated with respect to the transfer table 26, on which supports 27 a Petri dish 15 deposited in the transfer station 4 rests.

FIG. 5 shows the transfer table 26 with four supports 27 in detail. As can be seen, each support 27 forms a lateral approach surface 28 running obliquely, on which the Petri dish is centered. A support cushion 29 on which the Petri dish rests adjoins the approach surface 28. The support cushion 29 is preferably composed of a material with high cohesive friction (i.e., with higher cohesive friction than the residual material of the support 27), e.g., of rubber, so that the Petri dish (or the lid thereof) deposited thereon is not displaced as far as possible during the manipulations described below.

In the embodiment according to FIG. 2, the transfer station 4 is arranged in a vertically moveable manner on a lift 30 with drive 31. In contrast thereto, the transfer station 4 in the embodiment according to FIG. 1 is not adjustable in height—instead the transfer device 3 is arranged on a lift 30' in a height-adjustable manner. Both variants are possible. The important thing is that the transfer device 3 (or the gripper thereof described below) can be moved vertically with respect to the transfer station 4.

The transfer device 3 has a rail 32 along which a head 33 can be moved along a horizontal axis 34. To this end, a horizontal drive 35 is provided.

Figure 3:
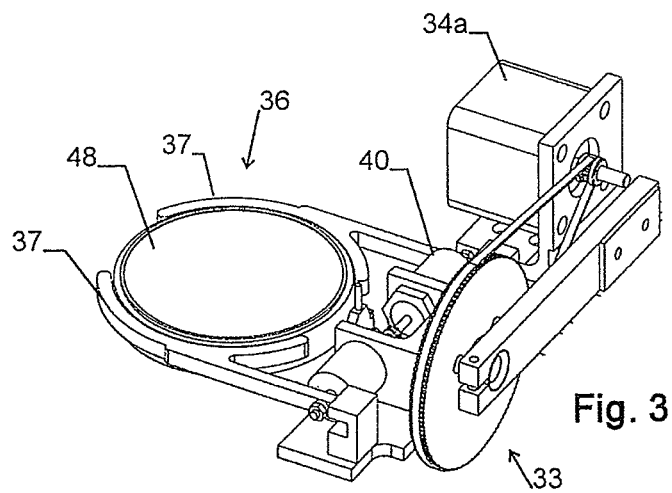
FIG. 3 illustrates a part of the transfer device.

The head 33, the structure of which can be seen from FIGS. 2 and 3, can be pivoted about an axis parallel to the axis 34, for which purpose a turning drive 34a is provided, and bears a gripper 36 with two fingers 37. The gripper 36 can thus be pivoted about a horizontal axis and can be moved vertically with respect to the transfer station 4.

The gripper 36 has a finger drive 40, with which the two fingers 37 can be moved with respect to one another, e.g., in a linear movement.

FIG. 4 shows a possible structure of a gripper 36 in detail. Each finger 37 has a body 38, wherein the two bodies 38 can be moved with respect to one another. At least three elevations 43 directed against one another are provided on the fingers 37, in order to grasp the sidewalls of the Petri dish 15. These are used to act on the wall of the Petri dish 15 at defined points (or along defined surface lines) so that the Petri dish 15 can be picked up safely and without play.

Preferably, at least one of the elevations 43 is attached resiliently to the respective finger 37. In the embodiment according to FIG. 4, to this end a spring mounting 39 embodied as a leaf spring is arranged on one of the fingers 37, which spring mounting 39 in turn holds a curved base part 42. At least one of the elevations 43 is arranged on the base part 42. In the example shown, two elevations 43 are arranged on the base part 42.

FIG. 10 shows an alternative embodiment of the gripper 36, in which both fingers 37 each have a spring mounting 39, which respectively bears a base part 42. In this case each base part 42 is equipped with at least two elevations 43, since the spring mountings 39 permit a certain tilting of the base parts 42, and thus, also four elevations 43 can be pressed free from play against a not quite round Petri dish 15.

In order to understand the function of the present device, firstly the design of the Petri dishes 15 must be explained. A Petri dish of this type can be seen in FIG. 2. It has a base 48 and a lid 49. As mentioned at the outset, the sample to be tested is located on the base 48, e.g., in a nutrient substrate adhering to the base 48, but the Petri dish 15 is supported in the storage device such that the base 48 is above the lid 49, i.e., bears against the lid 49. For the analysis of the Petri dish 15 in the inspection device described in more detail below, the base 48 must be separated from the lid 49 and rotated about a horizontal axis by 180°.

The base 48 has a round base area 52, on the circumference of which a peripheral, approximately cylindrical base wall 53 is provided. The lid 49 in turn likewise has a round lid area 55, on the circumference of which a cylindrical lid wall 56 is provided. The inner diameter of the lid wall 56 is somewhat larger than the outer diameter of the base wall 53. When the base 48 and the lid 49 are joined together, the base wall 53 engages in the lid wall 56 and rests against the lid area 55.

As mentioned, the Petri dishes 15 are stored in the storage locations of the storage device 1 with the lid 49 downwards. The handling device transfers the Petri dishes 15, without turning them over, between the storage locations and the transfer station 4. The Petri dishes 15 thus come to rest in the transfer station 4 with the lid 49 downwards. Now the gripper 36 is placed from above over the base 48 of the Petri dish 15. The fingers 37 are moved towards one another so that they grasp the base 48 of the Petri dish 15 on the base wall 53. Now the gripper 36 can be lifted relative to the transfer station 4 so that it draws the base 48 out of the lid 49. If at this time a drop detaches itself from the base 48, it falls into the lid 49.

Now the gripper 36 with the held Petri dish 15 is turned over. This takes place vertically above the lid 49 lying in the transfer station 4, so that also in this phase any drops detaching themselves from the base 48 fall into the lid 49. Preferably, the base 48 is not moved away from above the lid 49 until it has been turned by more than 90°.

Now the gripper 36 with the held and turned lid 48 can be moved to the inspection device 2 with the aid of the horizontal drive 35. In the present embodiment, it is an optical inspection device with a camera 50, which can provide an image of a Petri dish 15 arranged in a measurement position 51. The measurement position 51 is located between the camera 50 and a light source 52 in order to generate photos in transmitted light.

The lid 48 held and turned can be moved to the measurement position 51 with the gripper 36. To this end, the horizontal drive 35 is used, with which the head 33 can be moved along the rail 32. The device is embodied thereby such that the lid 48 of the Petri dish is held by the gripper 36 during the inspection by the inspection device. It is therefore not necessary for the lid 48 to be deposited in the inspection device 2. This accelerates the procedure. Since the gripper 36 grasps the lid 48 only on the periphery, it does not interfere with the inspection process.

As already mentioned, the Petri dishes 15 are stored in the storage device 1 in storage racks 14. An advantageous storage rack is shown in FIGS. 6 and 7.

The storage rack shown is essentially shaped from a single metal sheet, which has been cut to length and curved in a suitable manner. In particular, the metal sheet forms a vertical rear wall 60 and two vertical sidewalls 61. Lateral storage compartments 63 for holding the Petri dishes are arranged at least on the sidewalls 61, preferably also on the rear wall 60. These are formed by curved-back tongues of the sheet metal of the rear and sidewalls.

The rear wall 60 merges respectively via a transition region 64 into each sidewall 61. This transition region runs obliquely to the sides in the embodiment according to FIGS. 6 and 7 so that volume that is not needed in the rear region of the storage racks 14 by the round Petri dishes 15 can be released. This makes it possible for a denser packing of the storage racks 14 in a circle, as illustrated in FIG. 1, in that the storage racks can move closer together in the circle.

Since Petri dishes 15 have a typical diameter in the order of magnitude of 9 cm, the transition region 64 can have a flat section 66 running vertically, the extension of which, perpendicular to the longitudinal axis (vertical axis) of the storage rack 14, is at least 2 cm.

Since Petri dishes 15 are round, the transition region 64 can fundamentally also run in a rounded manner, as is shown by a dotted line 66' in FIG. 7. In this case, when the radius of curvature of the transition region 64 corresponds approximately to that of the Petri dishes 15, an even denser packing of the storage racks 14 is possible, however with somewhat higher production expenditure. In this case the radius of curvature of the transition region on average can be at least 2 cm, preferably at least 5 cm.

As can be further seen from FIGS. 6 and 7, the base 67 and the lid 68 of each storage rack 14 also merge in one piece into the rear wall 60, and are produced by bending from the same metal sheet as the rear wall 60 and the sidewalls 61.

Figure 8:
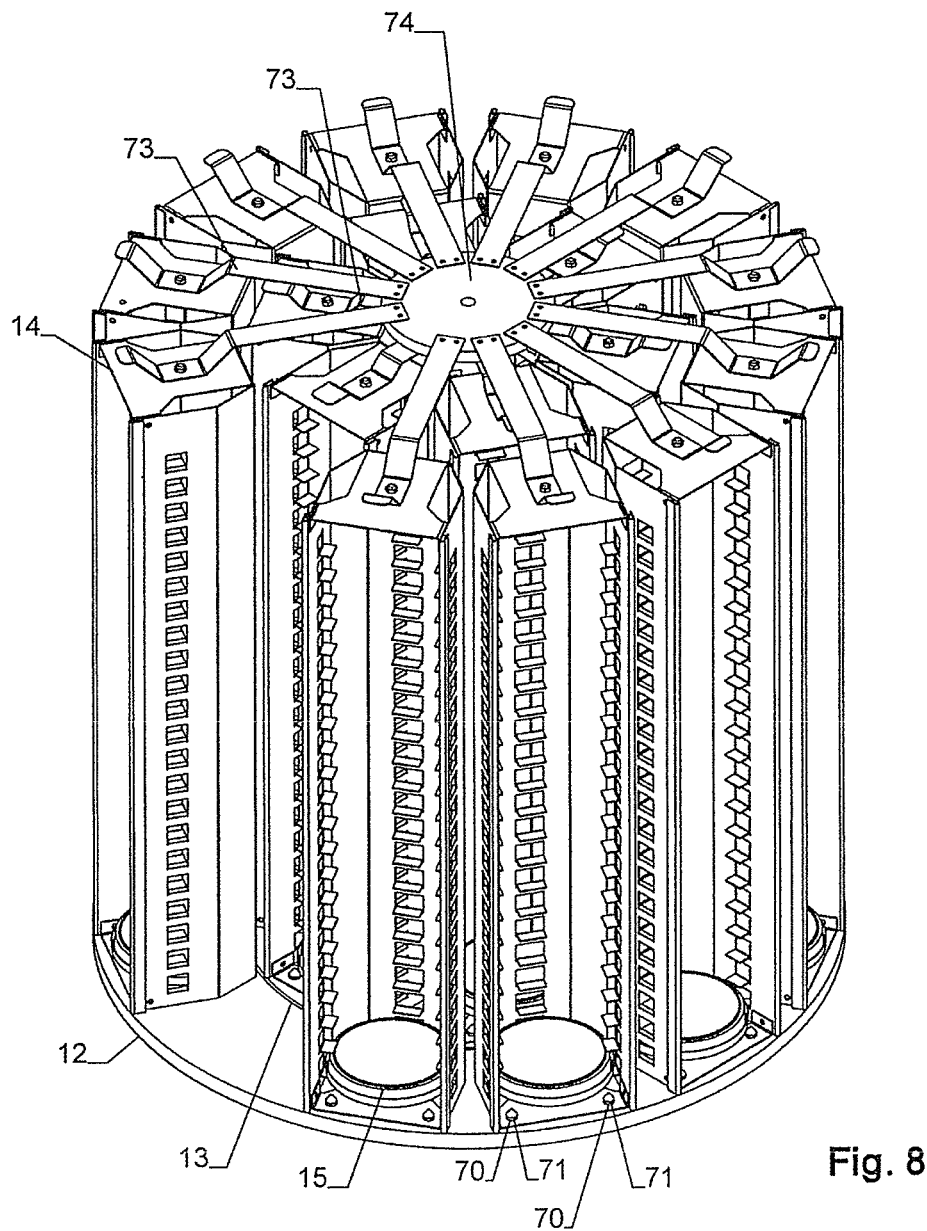
FIG. 8 illustrates a fastening variant for the storage racks.

The storage racks 14 can be attached in the storage device 1 in principle in any suitable manner. A preferred attachment variant is shown in FIG. 8. Here one or more openings 70 are provided in the base 67 (see FIG. 7), in which pins 71 engage. The pins 71 are connected to the substrate on which the respective storage rack 14 stands. In the embodiment according to FIG. 8, this substrate is formed by one of the carousels 12 or 13. The pins 71 taper conically upwards.

From the top the storage racks are held by resilient tongues 73 running in a radial manner, which are attached to a center region 74 of the storage device 1. The tongues 73 are advantageously biased in a resilient manner and press from above on the storage racks 14. In embodiments, the tongues 73 can be screwed to the storage racks 14.

FIG. 9 shows a second embodiment of the transfer device 3. It differs from that according to FIG. 1 in that two transfer stations 4 are provided with respectively one individual transfer table 26 one above the other. These can be moved vertically on the lift 30, preferably with a common lift drive 31. Each of the transfer stations 4 can be moved to the height at which it can interact with the gripper 36 and the handling device 5. Thus, for example, a first Petri dish 15 can be analyzed while its lid 49 lies in the one transfer station 4, while the handling device 5 removes a Petri dish 15 from the other transfer station 4 or feeds a Petri dish 15 to it.

Figure 11:
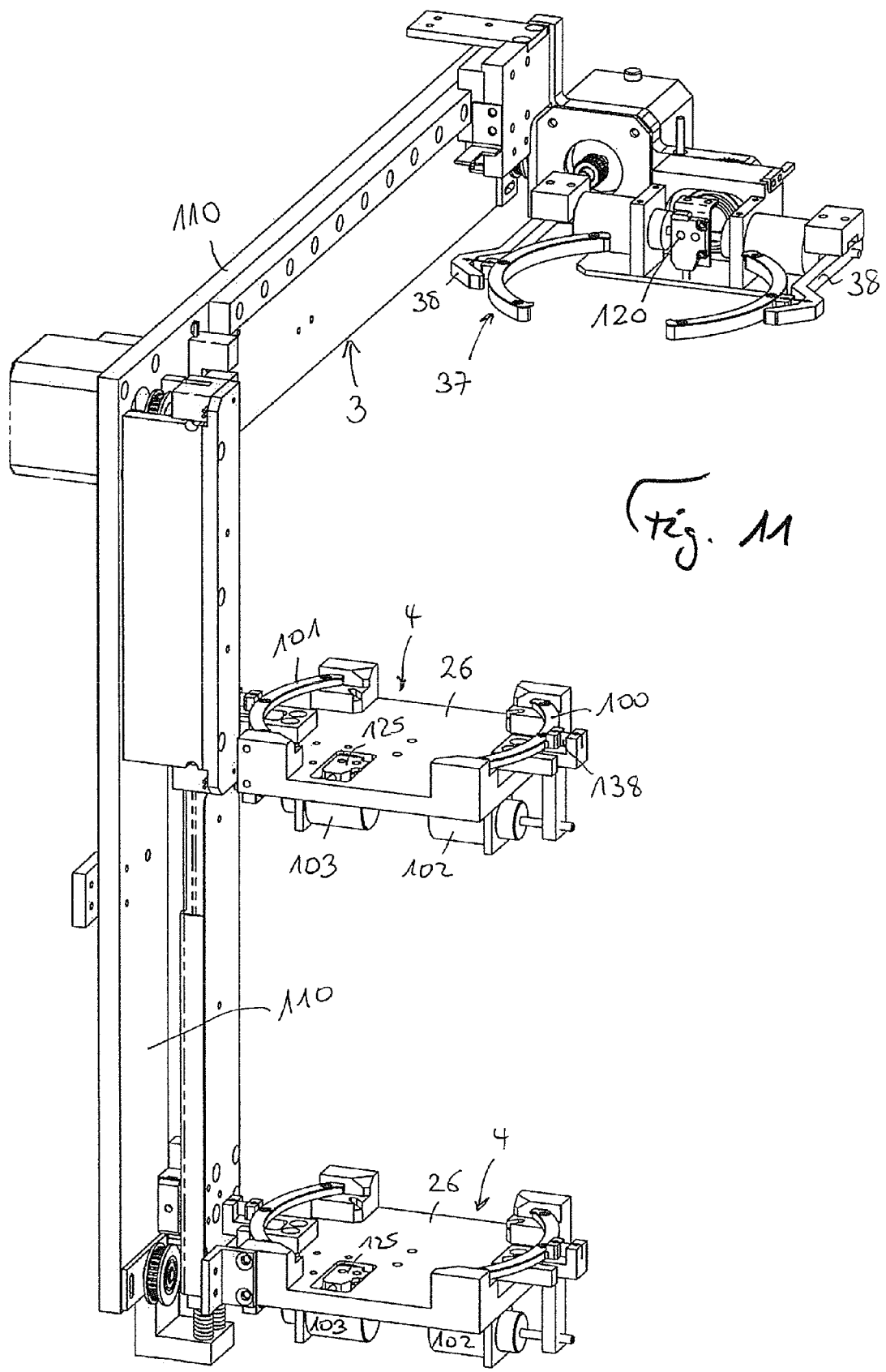
FIG. 11 illustrates a representation of a further transfer device with two transfer stations to explain further preferred embodiments.

In a preferred embodiment according to FIG. 11, at least one fixing element 100 for the lid 49 of the Petri dish 15 is provided on the at least one transfer station 4, two transfer stations 4 being shown in this figure. The fixing element 100 is embodied such that the lid 49 can be temporarily fixed in a controlled manner by the fixing element 100. This can prevent a lid 49 from "sticking" to the base of the Petri dish 15 from being carried along by the gripper 36 when the gripper 36 lifts the base 48. In the example shown, at each transfer station 4 or at the transfer table 26 thereof respectively two fixing elements 100 and 101 are arranged, which, like the fingers of the gripper 36 for the base 48 of the Petri dish 15, can contact the lid 49 at its edge in a driven and controlled manner and fix the base 48 therewith. In the figure, the drives 102 and 103 for the fixing elements 100 or 101 can be seen, which fixing elements 100 and 101 are actuated by the control of the device such that the fixing elements 100 and 101 hold or fix the lid 49 when the gripper 36 grasps and lifts the base 48. The fixing elements 100 and 101 are preferably arched and can be pivoted in the horizontal plane or in a plane coplanar to the plane of the transfer table 26 in order to be able to adapt themselves to the lid 49. A pivotability can thus be produced with a leaf spring as is explained below with preferred fingers of the gripper 36 in FIGS. 12 and 13.

It is further shown in FIG. 11 that the transfer device 3 has a common carrier plate 110 for the transfer station 4, in particular for both transfer stations 4, and the gripper 36, on which carrier plate 110 the transfer station 4 or the transfer stations 4 and the gripper 36 are arranged, wherein this is in particular a one-piece carrier plate 110 and in particular an L-shaped 110 carrier plate. This results in a very simple assembly and holds the referenced parts of the transfer device 3 in a simple manner in a precisely defined position to one another, which cannot shift, which is important for the repeat accuracy of the sequences.

It is further preferred that the transfer device 3 in the region of the gripper 36 has an optical sensor 120 that can be switched off temporarily in a controlled manner, which is designed and arranged for the detection of the presence or absence of the Petri dish 15 in the gripper 36. The optical sensor 120 is provided for emitting corresponding signals to the control of the transfer device 3. Switching off the optical sensor 120 by the control makes it possible to avoid disruption of the inspection of the Petri dish 15 by the light influence of the optical sensor 120.

Preferably, a further sensor 125 for detecting the presence or absence of the lid 49 in the transfer station 4 is provided on each transfer station 4, which sensor 125 is provided in particular for the control of the fixing elements 100 and 101.

The transfer device 3 is preferably embodied such that with the gripper 36, the base position thereof is the grasping state so that in the event of a disruption, e.g., with a brief loss of power, the laboratory object or the base 48 of the Petri dish 15 held by the gripper 36 is nevertheless held. The drive of the gripper 36 thus acts such that it drives the gripper 36 to release and that the drive does not need to be active for holding. In the case of the fixing elements 100 and 101, however, the base position is open, so that a laboratory object can at least be deposited or placed on the table 26 and only fixing requires the active drive.

Figure 13:
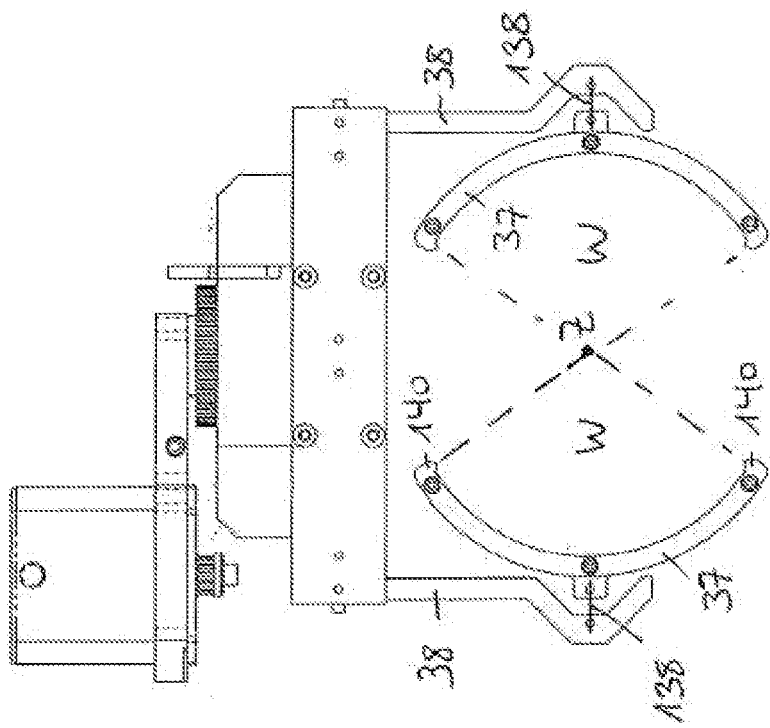
FIG. 13 illustrates the gripper from FIG. 12 in plan view from above.
Figure 12:
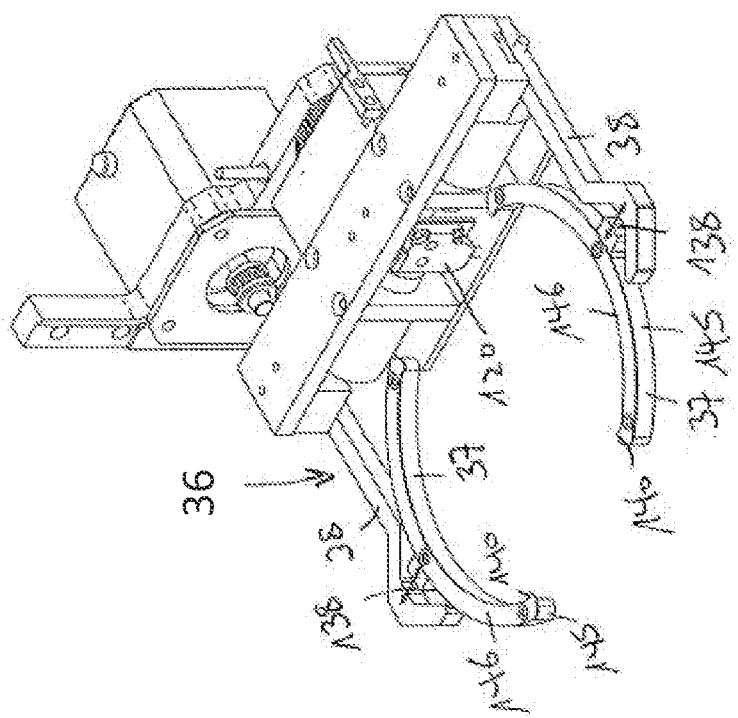
FIG. 12 illustrates a further embodiment of a gripper in diagrammatic view.

Preferred embodiments of the gripper are explained based on FIGS. 12 and 13, wherein the gripper 36 has at least two fingers 37, which are arranged one each on a body 38, wherein the bodies 38 can be moved in a controlled driven manner towards one another and away from one another, as has already been explained. It can be seen that each finger 37 is attached to the associated body 38 in a manner pivotable in a horizontal plane, which is symbolized by the curved arrows in FIG. 12. It is particularly provided thereby that each finger 37 can move independently into an unpivoted centered base position, which renders possible in a simple manner a good adjustment to each new Petri dish 15 to be grasped. This is preferably solved in that the respective finger 37 is attached by a vertically upright leaf spring 138 at a point on the associated body. The leaf spring 138 permits the pivot motion in the horizontal plane and only in the horizontal plane and causes the resetting.

Also in this embodiment, the fingers 37 of the gripper 36 are designed and arranged for an essentially punctiform contact of the Petri dish 15, wherein in particular a punctiform contact by the end regions 140 of the fingers is preferred, as can be seen in the figures. As shown in FIG. 13, it is preferred thereby that the gripper 36 is embodied such that the size of the angle W from the center Z of the grasp region to the outermost contact parts, provided and arranged for contacting the Petri dish 15, of the fingers 37 of the gripper 36 is 80 angular degrees to 120 angular degrees and preferably 85 degrees to 100 degrees and preferably approximately 90 degrees. In particular the value of approximately 90 degrees is preferred for a secure grasp and hold and release.

Furthermore, it is advantageous for the execution and maintenance if the fingers 37 of the gripper 36 are formed by a base part 145 and an interchange part 146 releasably attached thereto. The interchange part 146 is thereby designed for the punctiform contact. The base part 145 can be formed of a light metal, in particular aluminum, and the interchange part 146 of steel, in particular spring steel.

Figure 14:
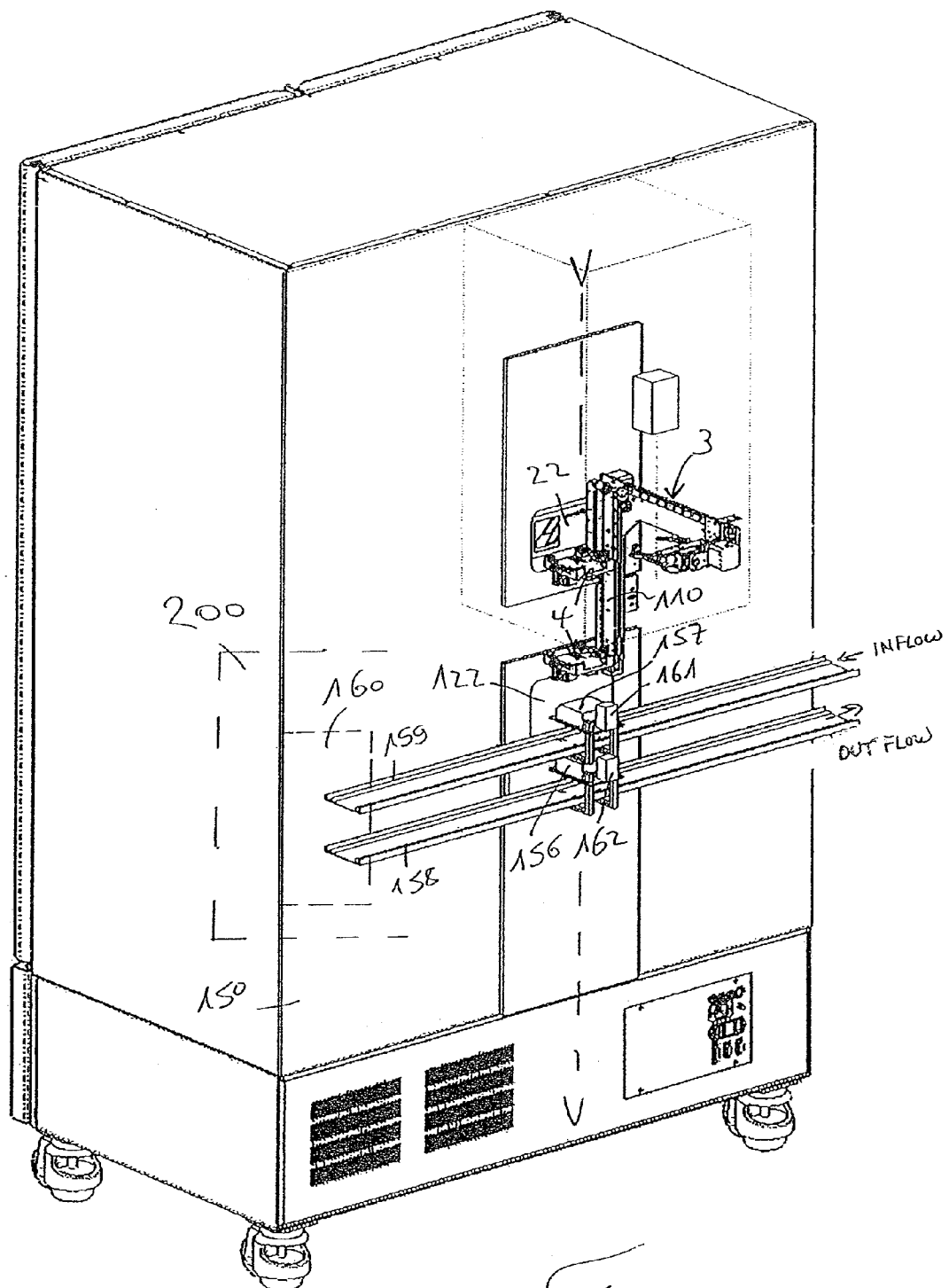
FIG. 14 illustrates a view of a preferred variant of the device and a part of a laboratory device interacting therewith.
Figure 15:
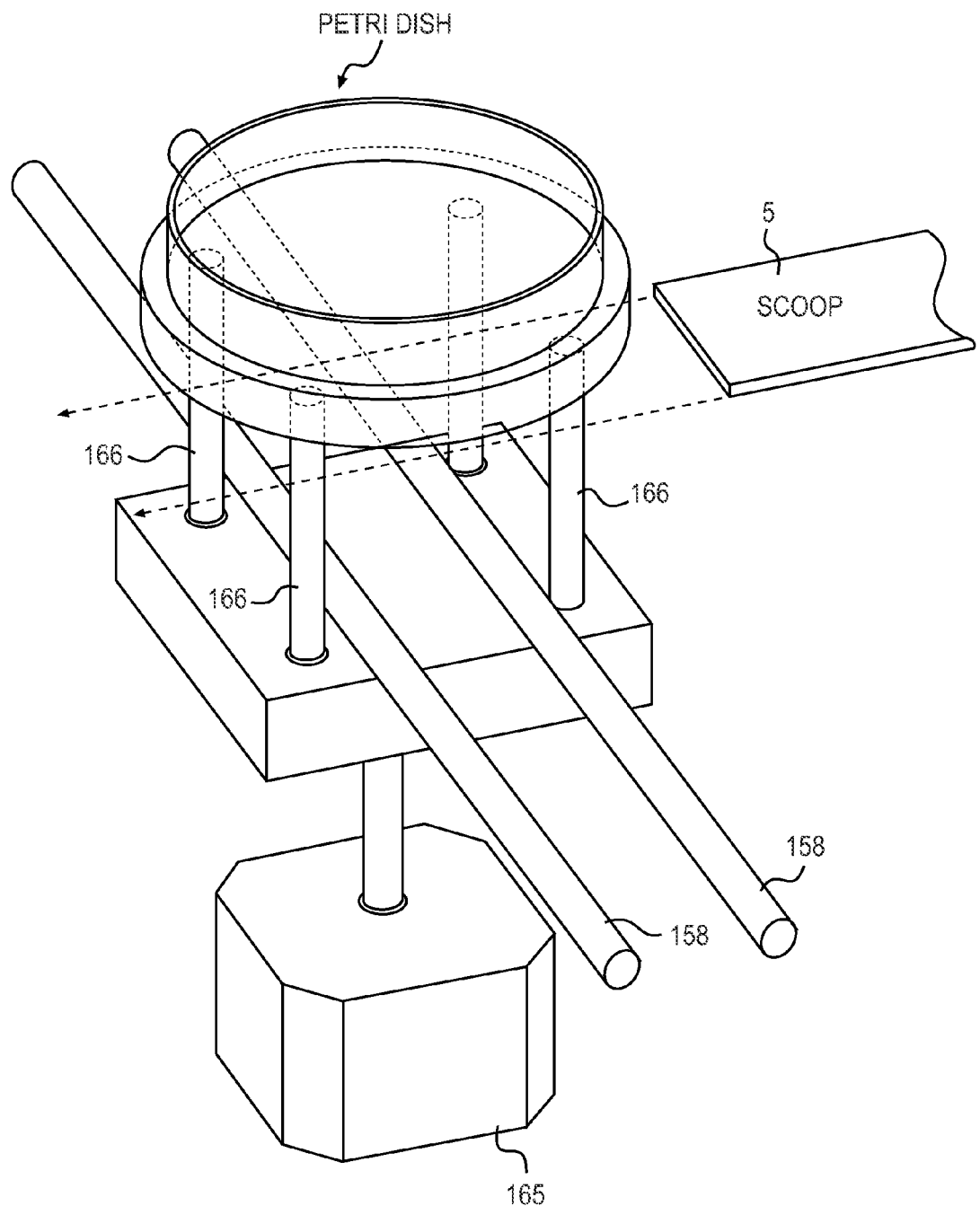
FIG. 15 illustrates a diagrammatic view of a lifting device.

Preferably, the device (i.e., the storage device 1, the inspection device, the transfer device 3, the transfer station 4, and the handling device 5) is incorporated into a further laboratory environment, and in this context it is preferred if the device, as shown in FIG. 14, is embodied such that the storage device 1 has a second auxiliary door 122 on its wall 150, on which the transfer device 3 is found, through which auxiliary door 122 the supply or removal of Petri dishes 15 to or from of the storage device 1 is carried out by the handling device 5 and a transport arrangement 155 located outside the storage device 1 on its wall 150, wherein the second auxiliary door 122 in particular lies in the same vertical axis V as the first auxiliary door 22, in particular beneath the first auxiliary door 22. This permits the charging with Petri dishes 15 and the removal of Petri dishes 15 in interaction with the laboratory environment and the inspection and provides a speed advantage in the management of the laboratory objects or Petri dishes 15. As shown, the transport arrangement 155 has two lifting devices 156, 157 lying vertically one above the other and driven in a controllable manner, by which Petri dishes 15, independently of one another can be lifted from or deposited on two conveyor belts 158, 159 arranged one above the other. A lifting device 156 is shown by way of example in FIG. 15. According to FIG. 14, this lifting device 156 is used for discharging Petri dishes 15, which are removed from the storage device 1 through the second door 122 by the scoop of the handling device 5. Four columns 166 can be lifted by the underside drive 165 thereof and the Petri dishes 15 lying on the scoop can be supported from below so that the scoop of the handling device 5 can be drawn back again and the Petri dish 15 bears against the columns 166. The columns 166 are then lowered again and place the Petri dish 15 on the conveyor belt 158, which here is formed by two separate belts driven synchronously. A control and a drive 160 of the conveyor belt 158, which elements belong to the superordinate laboratory environment 200, which is indicated in FIG. 14, then remove the Petri dish 15, e.g., for disposal. The same procedure basically applies to the other lifting device 157 for the supply of Petri dishes 15 to the storage device 1, wherein, however, here a Petri dish 15 is supplied by the conveyor belt 159, lifted by the lifting device 157, scooped by the scoop of the handling device 5, and taken by the scoop of the handling device 5 by lowering the lifting device 157, and then is moved into the storage device 1 through the second auxiliary door 122. For the control of these processes, it is preferred for the lifting device to have respectively one sensor by which the presence or absence of a Petri dish 15 can be established.

According to FIG. 16, it is preferred if two carousels 12', 13' arranged separately from one another and next to one another, are provided in the storage device 1, which carousels 12', 13' can be served by a common handling device 5.

The explained laboratory device, with a device according to the invention, wherein the laboratory device has a control and two conveyor belts 158, 159 lying one above the other and driven in a controllable manner, wherein the conveyor belts 158, 159 are arranged and can be controlled such that they are designed for interaction with the lifting devices 156, 157 in order to feed Petri dishes 15 into the laboratory device or to remove them therefrom, renders possible a particularly efficient and rapid handling of the Petri dishes 15.

While preferred embodiments of the invention are described in the present application, it should be noted that the invention is not restricted thereto and can also be carried out in a different manner within the scope of the following claims.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

The invention claimed is:

1. A device for storing and handling Petri dishes having a base with a base wall arranged on a circumference of the base, and a lid, the device comprising:
    a storage device structured and arranged for storing the Petri dishes in an upside-down orientation so that respective lids are oriented below their respective bases;
    an inspection device structured and arranged for automatic inspection of the Petri dishes without their respective lids; and
    a transfer device structured and arranged for transferring the Petri dishes between the storage device and the inspection device,
    wherein the transfer device comprises a gripper structured and arranged to laterally grasp the base wall of a respective base,
    wherein the transfer device further comprises at least one transfer station structured and arranged for holding the respective Petri dish in the upside-down orientation, from which the gripper can grasp the respective base,
    wherein the transfer device further comprises a turning drive structured and arranged to rotate the gripper with a held base of a Petri dish vertically above the lid lying in the transfer station, and
    wherein the turning drive is structured and arranged to rotate the gripper with a held base part of a Petri dish vertically above the lid lying on the transfer station by more than 90°.

2. The device according to claim 1, wherein the transfer device further comprises a lift drive structured and arranged to displace the gripper vertically relative to the transfer station.

3. The device according to claim 1, wherein the transfer device further comprises a horizontal drive structured and arranged to move the gripper to and from the inspection device for inspection.

4. The device according to claim 1, wherein the at least one transfer station comprises two transfer stations, both of which are moveable.

5. The device according to claim 4, further comprising a common lift drive for the two transfer stations.

6. The device according to claim 1, wherein the transfer device is structured and arranged to hold the base with the gripper during the inspection by the inspection device.

7. The device according to claim 1, wherein the at least one transfer station further comprises at least one fixing element for the lid of the Petri dish, which is structured and arranged to temporarily fix the lid in a controlled manner.

8. The device according to claim 7, wherein the at least one fixing element comprises an arched fixing element.

9. The device according to claim 7, wherein the at least one transfer station further comprises a transfer table, and wherein the at least one fixing element is structured and arranged on the transfer table.

10. The device according to claim 7, wherein the at least one fixing element comprises two fixing elements.

11. The device according to claim 1, wherein the transfer device comprises a common carrier plate on which the at least one transfer station and the gripper are arranged.

12. The device according to claim 11, wherein the at least one transfer station comprises two transfer stations.

13. The device according to claim 11, wherein the common carrier plate is a one-piece carrier plate.

14. The device according to claim 11, wherein the common carrier plate is an L-shaped carrier plate.

15. The device according to claim 7, wherein the at least one fixing element is structured and arranged such that its base position is an open, non-fixing position.

16. The device according to claim 1, wherein the gripper comprises at least two fingers, which are each structured and arranged on respective bodies, wherein the bodies are structured and arranged to be moved towards one another and away from one another in a controlled driven manner, and wherein each finger is attached to a respective body in a manner to be pivotable in a horizontal plane.

17. The device according to claim 16, wherein each finger is attached to a respective shaft, and is structured and arranged for centering itself automatically into an unpivoted base position.

18. The device according to claim 17, wherein each finger is attached to the respective shaft by a rear side of each finger via a respective leaf spring.

19. The device according to claim 16, wherein the fingers of the gripper are structured and arranged for an essentially punctiform contact with the Petri dish.

20. The device according to claim 19, wherein the fingers comprise end regions, and the punctiform contact is provided by the of the end regions of the fingers.

21. The device according to claim 16, wherein the fingers comprise:
    a base part; and
    an interchange part releasably attached to the base part,
    wherein the interchange part is structured and arranged to provide an essentially punctiform contact with the Petri dish.

22. The device according to claim 21, wherein the base part is formed of a light metal and the interchange part is formed of steel.

23. The device according to claim 22, wherein the light metal comprises aluminum.

24. The device according to claim 22, wherein the steel comprises spring steel.

25. A device for storing and handling Petri dishes having a base with a base wall arranged on a circumference of the base, and a lid, the device comprising:
    a storage device structured and arranged for storing the Petri dishes in an upside-down orientation so that respective lids are oriented below their respective bases;
    an inspection device structured and arranged for automatic inspection of the Petri dishes without their respective lids; and
    a transfer device structured and arranged for transferring the Petri dishes between the storage device and the inspection device,
    wherein the transfer device comprises a gripper structured and arranged to laterally grasp the base wall of a respective base, wherein the storage device comprises:
- a plurality of storage locations structured and arranged for storing the Petri dishes in the upside-down orientation so that respective lids are oriented below their respective bases; and
- a handling device structured and arranged to transport the Petri dishes between the storage locations and the transfer device.

26. The device according to claim 25, wherein the handling device is structured and arranged to transfer the Petri dishes between the storage locations and a transfer station without turning over the Petri dishes.

27. The device according to claim 26, wherein the storage locations are formed by a plurality of storage racks, wherein each storage rack has several storage locations one above the other.

28. The device according to claim 27, further comprising at least one carousel, wherein the storage shafts are arranged on the at least one carousel.

29. The device according to claim 26, wherein the handling device comprises two vertically moveable carriages.

30. The device according to claim 29, further comprising a common lift column, wherein the carriages are arranged above one another on the common lift column.

31. The device according to claim 25, wherein the gripper comprises two fingers moveable with respect to one another, and wherein the fingers have a plurality of elevations respectively directed against one another for acting on the base wall of the Petri dish.

32. The device according to claim 31, wherein the plurality of elevations comprise three elevations.

33. The device according to claim 31, wherein at least one of the fingers comprises a spring mounting bearing a base part, wherein at least one of the plurality of elevations is arranged on the base part.

34. The device according to claim 25, wherein the transfer device further comprises an optical sensor in the region of the gripper that can be switched off temporarily in a controlled manner, which sensor is structured and arranged for detecting a presence or absence of the base in the gripper.

35. The device according to claim 25, further comprising at least one transfer station comprising a sensor structured and arranged for detecting a presence or absence of the lid in the transfer station.

36. The device according to claim 25, wherein the gripper is structured and arranged such that its base position is a grasping condition.

37. The device according to claim 25, wherein the gripper is structured and arranged such that a size of an angle from a center of a grasping region to outermost contact parts of the fingers of the gripper, which are structured and arranged for contacting the base wall, is 80 to 120 degrees.

38. The device according to claim 37, wherein the angle is 85 to 100 degrees.

39. The device according to claim 37, wherein the angle is approximately 90 degrees.

40. A device for storing and handling Petri dishes having a base with a base wall arranged on a circumference of the base, and a lid, the device comprising:
- a storage device structured and arranged for storing the Petri dishes in an upside-down orientation so that respective lids are oriented below their respective bases;
- an inspection device structured and arranged for automatic inspection of the Petri dishes without their respective lids; and
- a transfer device structured and arranged for transferring the Petri dishes between the storage device and the inspection device,
wherein the transfer device comprises a gripper structured and arranged to laterally grasp the base wall of a respective base,
further comprising:
a handling device, and
a transport arrangement located outside the storage device on a wall of the storage device,
wherein the storage device comprises:
- a first auxiliary door on the wall of the storage device; and
- a second auxiliary door on the wall of the storage device through which a supply or removal of Petri dishes into or out of the storage device can be carried out by the handling device, and
wherein the transfer device is structured and arranged on the wall of the storage device.

41. The device according to claim 40, wherein the second auxiliary door lies in a same vertical axis as the first auxiliary door.

42. The device according to claim 40, wherein the second auxiliary door is arranged below the first auxiliary door.

43. The device according to claim 40, wherein the transport arrangement comprises two lifting devices lying vertically one above the other and driven in a controlled manner, by which Petri dishes, independently of one another, can be lifted from or deposited on two conveyor belts arranged one above the other.

44. The device according to claim 43, wherein each of the two lifting device has a respective sensor by which a presence or absence of a Petri dish can be established.

45. A laboratory device comprising the device according to claim 43, wherein the laboratory device comprises:
a control; and
two conveyor belts lying one above the other and driven in a controlled manner,
wherein the two conveyor belts are arranged and can be controlled to interact with the lifting devices in order to feed Petri dishes into the storage device of the device or to remove them therefrom.

* * * * *